(12) United States Patent
Creekmore et al.

(10) Patent No.: US 6,399,104 B1
(45) Date of Patent: Jun. 4, 2002

(54) PHARMACEUTICAL COMPOSITIONS

(75) Inventors: Joseph R Creekmore, Wilmington, DE (US); Susan J Corvari, Nashua, NH (US)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/581,612

(22) PCT Filed: Dec. 15, 1998

(86) PCT No.: PCT/GB98/03765

§ 371 (c)(1),
(2), (4) Date: Jun. 15, 2000

(87) PCT Pub. No.: WO99/32082

PCT Pub. Date: Jul. 1, 1999

(30) Foreign Application Priority Data

Dec. 18, 1997  (GB) .............................................. 9726735

(51) Int. Cl.[7] .............................. A61K 9/16; A61K 9/14; A61K 9/20; A61K 9/22; A61K 9/24

(52) U.S. Cl. ..................... 424/490; 424/489; 424/464; 424/465; 424/468; 424/472; 424/451; 424/456; 424/452; 424/457; 424/497

(58) Field of Search .................. 424/490, 489, 424/497, 464, 472, 468, 457, 465, 451, 452, 456

(56) References Cited

U.S. PATENT DOCUMENTS 5,319,097 A * 6/1994 Holohan et al. ............. 548/507
5,482,963 A * 1/1996 Holohan et al. ............. 514/415

* cited by examiner

*Primary Examiner*—Thurman K. Page
*Assistant Examiner*—Rachel M. Bennett
(74) *Attorney, Agent, or Firm*—Pillsbury Winthrop LLP

(57) ABSTRACT

A dry powder layering process for preparing pharmaceutical compositions of the leukotriene antagonist zafirlukast. The process forms coated beads suitable for sprinkling on to food and drink.

10 Claims, No Drawings

PHARMACEUTICAL COMPOSITIONS

This application is a 371 of PCT IG898/03765 filed Dec. 15, 1998.

The present invention relates to pharmaceutical compositions and in particular to pharmaceutical compositions containing the leukotriene antagonist zafirlukast. The invention also relates to processes for preparing such compositions and to their use in treating disease conditions mediated by leukotriene antagonists.

Zafirlukast is an orally administered leukotriene antagonist marketed under the trade mark 'ACCOLATE'. Zafirlukast is marketed for the treatment, including prophylactic treatment, of asthma and is presented as a tablet formulation containing 20 mg or 40 mg active ingredient. Asthma and related conditions are of particular concern in children and in the elderly. However, these patient groups have particular difficulties in swallowing medicaments in tablet form. The present invention provides a formulation of zafirlukast that permits easier administration and in particular should be of especial benefit for paediatric and geriatric patients.

Zafirlukast, which has the chemical name N-[4-[5-(cyclopentyloxycarbonyl)amino-1-methylindol-3-ylmethyl]-3-methoxybenzoyl]-2-methylbenzene, is known in a number of physical forms. U.S. Pat. No. 4,859,692 discloses this compound as Example 105. U.S. Pat. No. 5,319,097 discloses that this compound can exist in more than one physical form and that these physical forms have differing stabilities and bioavailabilities. Form A is disclosed as amorphous and as having good bioavailability. It is further disclosed that Form A tends to convert into Form B in the presence of water and that this is disadvantageous. It is unattractive to develop a formulation containing a mixture of physical forms with different bioavailabilities, especially where one form is physically unstable, because the effective dose of the compound can not be controlled properly. Form B is disclosed as a crystalline monohydrate with a defined X-ray powder diffraction pattern and a defined infra-red spectrum. Form X is disclosed as crystalline with a defined X-ray powder diffraction pattern.

U.S. Pat. No. 5,294,636 discloses particular formulations of Form X. Example 4 describes a tablet formulation prepared by a wet granulation process followed by drying, milling, blending and compression. Examples 2 and 3 describe pharmaceutical compositions of Form X that are suitable for administration by metered dose inhaler. Example 5 describes the micronisation of Form X to produce a powder which was extruded to form soft pellets; these pellets were free flowing and relatively dust free and, on shearing, broke back down to the original particle size distribution indicating that the pellets were suitable for inhalational use.

U.S. Pat. No. 5,319,097 discloses particular formulations of Form A. Example 3 describes a tablet formulation prepared by a wet granulation process followed by drying, milling, blending and compression. A particular feature of this Example is the presence of polyvinylpyrrolidone (also known as povidone). Example 5 describes a capsule formulation, a beadlet (spheroid) formulation and a powder formulation. The beadlet formulation is prepared by spraying an aqueous dispersion of polyvinylpyrrolidone and zafirlukast (in equal amounts) on to sugar spheres. This is an example of a suspension layering process, as zafirlukast, at the exemplified concentration would be partially soluble in the dispersion.

Pellets (also known as beadlets, spheroids, coated nonpareils, coated beads, coated seeds or granules) wherein a central core is surrounded by a layer containing drug may be prepared in a number of different ways. One method is to spray a solution of the drug optionally containing pharmaceutically acceptable ingredients on to the core material. Another method is to spray a suspension of the drug optionally containing pharmaceutically acceptable ingredients on to the core or seed material as was described in U.S. Pat. No. 5,319,097. A third method is to apply the drug and other pharmaceutically acceptable ingredients in the dry state. This third method is known as 'dry powder layering'. Usually dry powder layering requires the presence of water alone, or water with an aqueous binder or other solvent to facilitate the binding of the drug layer to the core material.

As stated hereinabove, zafirlukast exists in a number of physical forms and it is known that unwanted interconversion between certain forms can occur, especially in the presence of water. The three layering methods outlined above normally require water (as solvent, as the suspension medium, or to facilitate binding). Therefore, Applicants faced a problem in preparing pellets containing zafirlukast in particular in the amorphous form as none of the three methods was especially promising for preparing layered pellets suitable for pharmaceutical use. Unexpectedly, however, Applicants found that the pellets prepared by the dry powder layering method were stable and the physical forms of zafirlukast did not interconvert during the preparation and processing (including conditions of elevated temperatures and humidity) of the formulation. The preferred pellets of this invention are stable, non-friable and resist attrition. In particular, there is a tendency for any amorphous material (for example Form A) to convert to a crystalline form during processing conditions—as crystalline forms are generally the more stable forms. As stated hereinabove, it is unattractive to develop a formulation containing a mixture of physical forms with different bioavailabilities, especially where one form is physically unstable, because the effective dose of the compound can not be controlled properly.

Accordingly, the present invention provides a process for preparing a pharmaceutical composition which comprises applying amorphous zafirlukast and a binding agent and optionally other pharmaceutically acceptable ingredients to a plurality of cores to form layered pellets in which zafirlukast is present essentially in amorphous form. Amorphous zafirlukast is in dry form, appropriate for dry powder layering, immediately before the composition process.

Preferably the binding agent is an aqueous binding agent and in particular is water alone or water with other solvents.

Optionally a further binding agent may be present in the drug layer to assist the binding to the core material and to improve the strength of the pellets. Such additional binding agents may be any known to the person skilled in the art for this purpose. Preferred binding agents are polyvinylpyrrolidone and hydroxypropylmethylcellulose; of these polyvinylpyrrolidone is most preferred.

The cores are typically rotated or tumbled in a container to which amorphous zafirlukast and binding agent, optionally with other pharmaceutically acceptable ingredients, are added. The zafirlukast and binding agent are typically kept separate until they are added to the container; they are added to the container in a common feed or preferably in separate feeds. The separate feeds are generally simultaneous although the binding agent feed may commence slightly before the zafirlukast feed and may end slightly after the zafirlukast feed. As stated hereinabove, the function of the binding agent is to facilitate the binding of zafirlukast (and any pharmaceutically acceptable ingredients) to the core.

The pharmaceutical ingredients may be introduced to the container with the zafirlukast feed or with the binder feed or may be divided, selectively, into both feeds as the skilled person would understand. In general powders are fed into the container together and aqueous ingredients for example water are fed in separately. It is preferred that any aqueous feed is water or, if the aqueous feed contains other ingredients, it is in the form of a solution and not in the form of a suspension.

The nature of the central core of each pellet is not critical provided that it dissolves in aqueous media. Typically the central core material is a sugar sphere or non-pareil wherein the main ingredients are sugar, such as sucrose, and starch. Such sugar spheres or non-pareils are commercially available in a number of diameters under the trade marks 'Nu-core' and 'Nu-pareil'. Diameters available include 35–40 mesh (425–500 microns), 30–35 mesh (500–600 microns), 25–30 mesh (600–725 microns), 20–25 mesh (710–850 microns), 18–20 mesh (850–1000 microns), 16–20 mesh (850–1180 microns) and 14–18 mesh (1000–1400 microns). These are prepared from crystalline sucrose which is coated using sugar syrup and starch powder. In an alternative the central core is a sugar-free material, for example sorbitol, or microcrystalline cellulose; such cores are prepared in an analogous manner to sugar spheres. The cores would not usually contain zafirlukast but this is a possibility. The person skilled in the art will select the diameter of particles that is most appropriate considering the depth of surrounding layer that is intended and the desired diameter of the final pellet. Applicants prefer to use sugar spheres of 500–850 microns for example 30–35 mesh or 25–30 mesh.

Conventional pharmaceutical ingredients may be included in the processes of this invention. Examples of such pharmaceutical ingredients include bulking agents such as sugar, sorbitol and starch; binding agents such as polyvinylpyrrolidone and hydroxypropylmethylcellulose; disintegrants such as starch, croscarmellose sodium, sodium starch glycollate (A and B) and crospovidone; colourants such as titanium dioxide; flavouring agents; taste enhancers; sweeteners such as aspartame; preservatives; anti-oxidants; chelating agents; and surfactants. The binding agents are useful to assist binding to the core, to improve the strength of the pellet, and to aid the coating of the pellets with a further layer, if this is desired. Polyvinylpyrrolidone is available in various grades, known to those skilled in the art as K values. It is preferred to use Grades 29–32.

Typical pharmaceutical ingredients added in the processes of this invention include confectioner's sugar, starch and polyvinylpyrrolidone.

The ratio of ingredients may be varied, with regard to the desired dose, size and weight, as known to the skilled person. Suitably the ratio of layer to core is in the range 1:0.3 to 1:3.0 (w/w), more suitably in the range 1:1 to 1:2 (w/w). The ration of the zafirlukast to other ingredients in the layer is suitably in the range 1:1 to 1:10 (w/w), more suitably in the range 1:1 to 1:6 (w/w).

The dry powder layering process of this invention may be conveniently performed in any machine known to be suitable by those skilled in the art. For example the process may be performed in a rotary granulator, such as those sold by Glatt under the trade names Glatt GPCG-1, Glatt GPCG-5 and Glatt GPCG-60. [Handbook of Pharmaceutical Granulation Technology, ed. Dilip M. Parikh, published by Marcel Dekker Inc., 1997, page 291]. These granulators essentially consist of a fluidized bed dryer with the bottom of the product bowl consisting of a moveable and rotatable disc. The bowl contains ports from which the powder and aqueous binder are fed to the material in the bowl. Typical processing temperature/conditions for the layering phase, for the GPCG-60 apparatus are as follows: inlet air temperature: 30–40° C.; outlet air temperature: 25–40° C.; rotor speed 390 rpm; povidone solution flow rate: 100 gmin$^{-1}$; powder flow rate: 400 gmin$^{-1}$; processing time: 100 minutes.

The layered pellets are then dried at an elevated temperature, for example 30–60° C. preferably about 45° C., in the container.

These pellets comprise zafirlukast, essentially in amorphous form: that is substantially free of other physical forms of zafirlukast (for example as determined by X-ray diffraction data) preferably at least 90% by weight of zafirlukast is amorphous, more preferably 95% for example at least 96%, 97%, 98% or 99% is amorphous.

In another aspect, the present invention provides a pharmaceutical composition which comprises a plurality of pellets each of said pellets comprising:

a) a core; and b) a layer surrounding said core which layer contains amorphous zafirlukast substantially free of other physical forms, c) and optionally other pharmaceutically acceptable ingredients.

Preferred pharmaceutical compositions of this invention are those described hereinabove with reference to the process of this invention.

Preferably the layer surrounding the core comprises polyvinylpyrrolidone, more preferably wherein the amount of polyvinylpyrrolidone is not more than 50% by weight of the amount of zafirlukast, more preferably still wherein the amount of polyvinylpyrrolidone is in the range of 5–30% by weight of the amount of zafirlukast and in particular is about 10% by weight.

In a preferred aspect the process of the invention comprises separate feeds, one including amorphous zafirlukast and the other not including zafirlukast for example including aqueous polyvinylpyrrolidone. The non-zafirlukast feed, for example including aqueous polyvinylpyrrolidone, may be continued after the feed of zafirlukast to provide a coating layer on the pellets. This coating layer acts as a seal (a 'seal coat') and protects the pellets against attrition and friability, thereby maintaining the integrity of the formulation.

Thus, in a further aspect the present invention provides a pharmaceutical composition which comprises a plurality of pellets each of said pellets comprising:

a) a core;

b) a first layer surrounding said core which layer contains amorphous zafirlukast substantially free of other physical forms, preferably contains polyvinylpyrrolidone and optionally contains other pharmaceutically acceptable ingredients; and c) a second coating layer which does not contain zafirlukast.

In a further aspect, the pharmaceutical compositions of the present invention may be coated with a conventional coating layer for protection of the pellets or to provide sustained release pellets by application of a conventional sustained release coating such as 'Surelease' (a trade mark of Colorcon), 'Aquacoat' (a trade mark of FMC) or 'Eudragit' (a trade mark of Huls) which, in general, are cellulose derivatives such as hydroxypropylmethylcellulose or ethylcellulose or are methacrylic acid polymers. The sustained release coating may be applied using the apparatus described hereinabove or may be applied in a rotary granulator. The sustained release coating provides a generally uniform and constant rate of release over an extended period of time achieving a stable and desired blood (plasma) level of zafirlukast. The pellets may be substantially uniform or may vary in thickness and composition of the coating layer as well as in diameter.

Thus, in a further aspect the present invention provides a pharmaceutical composition which comprises a plurality of pellets each of said pellets comprising:
 a) a core;
 b) a first layer surrounding said core which layer contains amorphous zafirlukast substantially free of other physical forms, preferably contains polyvinylpyrrolidone and optionally contains other pharmaceutically acceptable ingredients; and
 c) a second coating layer which does not contain zafirlukast and which provides sustained release zafirlukast.

In one embodiment, the non-zafirlukast containing feed may be terminated simultaneously with the zafirlukast containing feed and the sustained release layer is applied subsequently. In another embodiment, the non-zafirlukast containing feed is continued after the zafirlukast feed to provide a 'seal coat' and the sustained release layer is applied subsequently.

Thus, a further aspect of this invention provides a pharmaceutical composition which comprises a plurality of pellets each of said pellets comprising:
 a) a core;
 b) a first layer surrounding said core which layer contains amorphous zafirlukast, polyvinylpyrrolidone and optionally other pharmaceutically acceptable ingredients;
 c) a second layer which does not contain zafirlukast; and
 d) a further layer which does not contain zafirlukast and which provides sustained release.

The pellets of the present invention typically range in size from 100 microns to 2 mm. Favourably they range in size from 200–1500 microns and preferably are in the range 400–1200 microns. Preferably the pellets are approximately uniform size and shape.

The pellets are normally sprinkled on to, or into, food or drink for easy consumption by the patient, but need not be taken with food or drink. The dose to be administered to the patient will depend on the condition being treated, the severity of that condition, the age and weight of the patient and the physician's personal preferences. In general the dose to be administered will be in the range of 0.1 mg/Kg to 10 mg/Kg, for example 0.2 mg/Kg to 5 mg/Kg, more particularly 0.5 mg/Kg to 2 mg/Kg.

In another aspect the present invention provides a method of treating patients in need thereof with a pharmaceutical composition according to the present invention which composition contains an effective amount of zafirlukast.

The pellets are packaged so that a defined dose of zafirlukast is administered, for example the pellets may be packaged in a sachet, in a capsule or in a metered delivery device. In one aspect a sachet is preferred wherein the patient tears open the sachet and sprinkles the pellets on to his or her food or drink. In another aspect a capsule is preferred; one example of such a capsule is that wherein the capsule is consumable and dissolves/breaks open having been taken orally by the patient. Another, more preferred example of a capsule is wherein the capsule is not intended to be consumed and the patient breaks open the capsule and sprinkles the pellets on to his or her food or drink. Examples of suitable sachets, consumable capsules (such as gelatin capsules) and non-consumable capsules (such as plastic) are known to persons skilled in the art. The dose of zafirlukast delivered in a sachet, capsule or metered delivery device may be varied as desired. Typically, 5–40 mg of zafirlukast is delivered in each unit dose, for example 10 mg, 20 mg or 40 mg of zafirlukast per capsule. The amount (by weight) of zafirlukast in the pellets may also be varied as desired; for example 100 mg weight of pellets may contain either 10 mg, 20 mg or 40 mg of zafirlukast.

The following Examples and data serve to illustrate the invention:

EXAMPLE 1

A 5% w/w solution of polyvinylpyrrolidone (150 g) in purified water USP (2850 ml) was made in a stainless steel vessel and mixed until dissolved. Sugar spheres (1000 g; mesh size 20–25) were placed into a rotor processor product container (I.E. Glatt GPCG-1) and the temperature was taken to 37° C. The polyvinylpyrrolidone solution was sprayed into the container at about 10 gmin$^{-1}$ at 37° C. Simultaneously, zafirlukast (100 g) was hand fed through an inlet into the product container at a rate of 10 gmin$^{-1}$. The addition of the polyvinylpyrrolidone solution was continued for 6 minutes after the addition of zafirlukast finished to provide a seal coat.

The resultant pellets were dried in the product container by raising the inlet air temperature to 45° C.

The pellets were encapsulated in size #2 hard gelatin capsules using an automatic encapsulator (I.E. Zanasi AZ/5) to a target fill weight of approximately 100 mg with 10% load of zafirlukast.

EXAMPLES 2–8

In a similar manner to that of Example 1, the following Examples were prepared. In these Examples, zafirlukast, starch and confectioner's sugar were charged to a blender (I.E. PK V-blender), blended and added via a powder feeder (rather than being fed by hand). The pellets were dried in the range 37–55° C.

In some Examples, the Glatt GPCG-1 was replaced by a Glatt GPCG-5 or Glatt GPCG-60 rotor processor container and the encapsulator was an H&K encapsulator.

|  | Example | | | | | | |
| --- | --- | --- | --- | --- | --- | --- | --- |
|  | 2 | 3 | 4 | 5 | 6 | 7 | 8 |
| Zafirlukast | 10.00 | 10.00 | 10.00 | 10.00 | 10.00 | 10.00 | 10.00 |
| Starch, NF | 10.00 | 4.20 | 7.20 | 7.20 | 7.20 | 7.20 | 7.20 |
| Confectioner's Sugar | 46.67 | 19.13 | 32.80 | 32.80 | 32.80 | 32.80 | 32.80 |
| Polyvinylpyrrolidone USP | 2.99 | 0.96 | 1.39 | 1.28 | 0.67 | 0.67 | 0.67 |
| Sugar Spheres (30/35 mesh) |  | 66.67 | 50.00 | 48.86 | 50.00 | 49.33 | 49.33 |
| Sugar Spheres (20/25 mesh) | 99.50 | 0.00 | 0.00 | 0.00 | 0.00 | 0.00 | 0.00 |
| Purified Water, USP | 56.72 | 23.04 | 33.38 | 33.38 | 16.57 | 16.67 | 13.84 |

Dissolution Studies

Initial dissolution studies, using 1% sodium dodecyl sulfate, on unencapsulated pellets showed satisfactory, rapid dissolution.

Stability Studies

The unencapsulated and encapsulated pellets of Example 7 were studied for 180 days at 25° C., 50° C. and at 40° C. (Relative Humidity 80%). X-Ray diffraction data showed no peaks—this indicated unchanged amorphous material with no observable conversion to crystalline material. This compares favourably with the results of the tablets of Example 4, Table 1 of U.S. Pat. No. 5,319,097. In that Table, 87%, 91% and 82% conversion to Form B (monohydrate) was recorded at 40° C. (Relative Humidity 80%) over 1, 2 and 3 months respectively.

EXAMPLES 9–24
Sustained Release Coated Pellets

Talc or magnesium stearate was dispersed in purified water using a homogeniser. This dispersion was added to a stirred suspension of Eudragit. The Eudragit suspension was stirred using a mixer. Further purified water was added to provide the coating composition. Surelease coating may be used in place of the mixture of Eudragit with talc or magnesium stearate.

Zafirlukast pellets [Example 7] (400 g) were heated to 24–35° C. in the product container of a fluid bed drier equipped with a Wurster column or rotor insert.

The pellets were coated with the coating composition [for example Eudragit NE30D (200 g) and talc (30 g) with purified water (370 g)] and dried at 24–30° C. to provide coated pellets.

In a further experiment, coating suspension (82 g) [Surelease (25.0% in purified water (85 g)] provided a weight gain of 5%.

What is claimed is:

1. A dry powder layering process for preparing a pharmaceutical composition which comprises a plurality of pellets, each of said pellets comprising:
   a) a core;
   b) a first layer surrounding said core which layer contains amorphous zafirlukast substantially free of other physical forms; and
   c) a second coating layer which does not contain zafirlukast; each layer optionally comprising other pharmaceutically acceptable ingredients, said process comprising the step of applying in separate feeds (1) amorphous zafirlukast in dry powder form and (2) a binding agent, and each feed optionally adding other pharmaceutically acceptable ingredients to a plurality of cores to form layered pellets, wherein the feed containing the binding agent commences slightly before the feed containing zafirlukast and ends slightly after the feed containing zafirlukast.

2. The process according to claim 1 wherein the binding agent is water or water in admixture with other solvents.

TABLE

Coating Suspension Composition:

| | Example: | | | | | | | |
|---|---|---|---|---|---|---|---|---|
| | 9 | 10 | 11 | 12 | 13 | 14 | 15 | 16 |
| Eudragit NE30D | 15% | 10% | 10% | 10% | 10% | | | |
| Talc | 10% | 5% | 5% | 5% | | | | |
| Magnesium Stearate, USP | | | | | 5% | | | |
| Surelease | | | | | | 15% | 15% | 15% |
| Purified Water, USP | 75% | 85% | 85% | 85% | 85% | 85% | 85% | 85% |
| Amount of Coating Suspension Applied | 120 g | 55.6 g | 135 g | 188 g | 55 g | 55 g | 134 g | 188 g |
| Percent Weight Gain | 7.5% | 2% | 5% | 7% | 2% | 2% | 5% | 7% |

| | Example: | | | | | | | |
|---|---|---|---|---|---|---|---|---|
| | 17 | 18 | 19 | 20 | 21 | 22 | 23 | 24 |
| Eudragit NE30D | 5% | 5% | 2.5% | 2.5% | | | 5% | 5% |
| Talc | 5% | 5% | 2.5% | 2.5% | | | 10% | 10% |
| Surelease | | | | | 25.3% | 25.3% | | |
| Purified Water, USP | 90.0% | 90.0% | 95.0% | 95.0% | 74.7% | 74.7% | 85.0% | 85.0% |
| Amount of Coating Suspension Applied | 80 g | 200 g | 160 g | 400 g | 34.5 g | 83 g | 60 g | 140 g |
| Percent Weight Gain | 2% | 5% | 2% | 5% | 2% | 5% | 2% | 5% |

EXAMPLE 25
Sustained Release Coated Pellets

A composition was prepared in the same manner as in Examples 2–8 with zafirlukast (19.74%), starch (24.29%), confectioners' sugar (5.37%), polyvinylpyrrolidone (1.28%) on sugar spheres (30/35 mesh) (49.36%) using purified water (62.17% of the powder weight).

These pellets (5000 g) were coated, in a manner similar to that of Examples 9–23, with a coating suspension (35 g) [Surelease (25.0%) and purified water (75%)]. The coating provided, after heating, coated pellets with a weight gain of 2%.

3. The process according to claim 1 which comprises applying a further binding agent being polyvinylpyrrolidone.

4. The process according to claim 3, wherein the first layer surrounding the core comprises polyvinylpyrrolidone in the range 5–30% by weight of the amount of zafirlukast present.

5. A pharmaceutical composition which comprises a plurality of pellets, each of said pellets comprising:
   a) a core;
   b) a first layer surrounding said core which layer contains amorphous zafirlukast substantially free of other physical forms; and
   c) a second coating layer which does not contain zafirlukast; each layer optionally comprising other pharmaceutically acceptable ingredients, wherein the composition is prepared by a process according to claim 1.

6. The pharmaceutical composition according to claim 5, wherein the first layer surrounding the core further comprises polyvinylpyrrolidone in the range of 5–30% by weight of the amount of zafirlukast present.

7. The pharmaceutical composition according to claim 5 wherein the second coating layer provides sustained release of zafirlukast.

8. The pharmaceutical composition according to claim 5 which comprises a further layer which does not contain zafirlukast and provides sustained release.

9. The pharmaceutical composition according to claim 5 packaged in sachet, capsule or metered delivery device.

10. The method of treating patients in need thereof with a pharmaceutical composition according to claim 5 which composition contains an effective amount of zafirlukast.

\* \* \* \* \*